United States Patent [19]

Schlaich

[11] Patent Number: 4,626,833

[45] Date of Patent: Dec. 2, 1986

[54] CIRCUIT ARRANGEMENT FOR CHECKING LIQUID FOOD FOR CONTAMINANTS

[76] Inventor: Robert Schlaich, Robert Bosch Str. 103, 7000 Stuttgart 1, Fed. Rep. of Germany

[21] Appl. No.: 678,058

[22] Filed: Dec. 4, 1984

[30] Foreign Application Priority Data

Jan. 4, 1984 [DE] Fed. Rep. of Germany ....... 3400129

[51] Int. Cl.⁴ ............................................. G08B 21/00
[52] U.S. Cl. .................................... 340/540; 324/439; 436/23; 340/603
[58] Field of Search ............... 340/540, 603; 324/446, 324/439; 436/20, 22, 23, 24; 422/62, 76, 74, 119

[56] References Cited

U.S. PATENT DOCUMENTS

| | | | |
|---|---|---|---|
| 1,479,087 | 1/1924 | Rice | 436/23 |
| 3,295,059 | 12/1966 | Coulter et al. | 324/439 |
| 3,593,119 | 7/1971 | Brum et al. | 324/439 |

Primary Examiner—Glen R. Swann, III
Attorney, Agent, or Firm—Fred Philpitt

[57] ABSTRACT

There is described a circuit arrangement for checking liquid food for contaminants which can be reliably operated fully automatically or at least by completely untrained staff. It comprises a conductivity measuring probe, whose output signal is processed by a transducer. From the output signal from the transducer there is substracted an amount in such a way that there is obtained a voltage which is independent of the individual nominal data of the batch. This independent constant voltage is made the reference point of a "window" of allowable deviations, the width of this window being independent of the individual batch data. The balancing of the circuit arrangement to the individual conductivity nominal value of the respective liquid food batch checked is the only change of voltages within the circuit arrangement, which takes place upon the transition from one liquid food batch to the next batch. This balancing may be effected automatically or manually by untrained operators who only have to bring about a specific state of a visual display by actuating a knob.

7 Claims, 3 Drawing Figures

CIRCUIT ARRANGEMENT FOR CHECKING LIQUID FOOD FOR CONTAMINANTS

BACKGROUND OF THE INVENTION

The invention relates to a circuit arrangement for checking liquid food for contaminants.

The checking of liquid food, for example of milk, beer, fruit juices or the like, during the processing and filling thereof has hitherto been effected by taking random samples. This does not reliably exclude any possibility of a contamination caused by acid, lye or water not being discovered and liquid food that is unfit for consumption reaching the consumer. Of particular urgency is the continuous automatic checking of multi-circuit filling plants, more especially milk filling plants in dairies. Plants of this kind are frequently operated in such a way that milk is filled in in one circuit, whilst the other circuit is cleansed by means of acids, lyes or the like. For greater flexibility the two circuits are interconnected, the connection being normally blocked by a solenoid valve. If this valve is not fully shut or is opened by mistake, then lye or acid can pass from the circuit which is in the process of being cleaned into the other circuit and thus into the milk.

Automatic checking of liquid food for contaminants by means of conductivity measurements has so far not been carried out since the nominal conductivity value can fluctuate considerably from batch to batch. For example, the basic conductivity of milk is subjected to seasonal fluctuations and the different grades of milk (homogenised milk, skimmed milk, buttermilk, etc.) have different basic conductivities. Consequently, it would be necessary to input for each new batch which is introduced into the monitored system not only the nominal value but also the upper and lower limits of the allowable deviations. However, such settings can only be effected by experts, who are not always available at any time in the processing establishments of liquid food.

SUMMARY OF THE INVENTION

It is the object of the present invention to provide a circuit arrangement of the kind mentioned at the beginning allowing the individual setting thereof to single food batches to be carried out by entirely untrained staff or else fully automatically.

According to the invention, this problem is solved in that the circuit arrangement comprises:

(a) A conductivity measuring probe which will be placed in or in the vicinity of the liquid food to be checked;

(b) a transducer which generates from the output signal from the measuring probe a voltage which is a measure of the respective conductivity detected;

(c) a subtraction stage, in which an individual reference voltage adapted to the checked food batch is subtracted from the transducer voltage in such a way that the output signal from the subtraction stage has a constant value which is independent of the food batch;

(d) a measuring amplifier which amplifies the output signal from the subtraction stage to an extent that is independent of the food batch;

(e) a first comparator which compares the output signal from the measuring amplifier with a first comparison voltage which represents an upper allowable conductivity nominal value deviation which is independent of the food batch, the first comparator triggering an alarm if the first comparison voltage is exceeded;

(f) a second comparator which compares the output signal from the measuring amplifier with a second comparison voltage which represents a lower conductivity nominal value deviation which is independent of the food batch, the second comparator triggering an alarm if the second comparison voltage is not attained.

The invention is based on the realisation that the allowable "window width", namely the allowable deviations of the conductivity from a specific nominal value associated with the individual batch, is independent of the magnitude of this nominal value, in other words that the checking of all the batches of a liquid food, provided these belong to a uniform class (e.g. milk), can be effected with a window width of the same absolute magnitude. If a reference voltage is thus subtracted from the voltage representing the respective conductivity of the individual batch in such a way that there comes about a batch-independent voltage, then the operating voltages of the following circuits can be left unchanged. The batch-dependent reference voltage variation necessary for attaining this purpose is the only change in the circuit arrangement operating magnitudes set and, as will be made clear hereinafter, can be carried out without any special knowledge or else automatically.

There may be associated with each comparator a separate alarm unit. In this way, it is possible to discern whether the allowable window is exceeded in the upward or downward direction. From this there can be generally deduced a first clue as to the type of contamination: A higher conductivity is generally based on a contamination caused by acids or lyes, whilst the cause of a lower conductivity is generally dilution caused by water.

Alternatively, the output signals from the two comparators may be fed to the same alarm unit via an OR-gate.

The allowable upward deviation from the conductivity nominal value represented by the first comparison voltage should be less than the downward deviation from the conductivity nominal value represented by the second comparison voltage. This, too, is based on the above-mentioned fact that higher conductivity values are based on the more dangerous contamination caused by acids or lyes, whilst lower conductivity values are attributable to the harmless dilution caused by water.

The unit which generates the reference voltage fed to the subtraction stage may be actuatable by hand, when a visual display will be provided, which gives a display when the output voltage from the subtraction stage has reached the constant value which is independent of the food batch. Therefore, when a new batch of liquid food is introduced into the monitored system, all the operator needs to do is to bring about a specific state of the visual display on a knob, for example to place the indicator of a measuring instrument into a specific position. No special knowledge whatsoever is required for this purpose.

Alternatively, the unit generating the reference voltage fed to the subtraction stage may comprise a self-balancing loop which can be inserted via a switch between the subtraction stage output and the subtraction stage reference input, the switch being closed when a new liquid food batch is introduced into the monitored system until balancing is completed and then being re-opened. In this development of the invention, the balancing or "standardisation" of the circuit arrangement to the nominal conductivity value of the respective batch checked is thus effected fully automatically so that it is not only impossible for any faulty operation to occur but the re-setting of the circuit arrangement to the batch cannot be forgotten. This applies, in particular, if the closure of the switch is forcibly coupled to a process which is necessary in any case when a new batch is introduced into the monitored system, for example to the opening of a solenoid valve.

The self-balancing loop may comprise:

(g) an amplifier, to which the output signal from the subtraction stage can be fed;
(h) a motor, which is connected to the amplifier output;
(i) a potentiometer, which forms part of a voltage divider and whose wiper is mechanically coupled to the motor.

In the case of this development, the motor is fed with a voltage as long as the output signal from the subtraction stage has not reached the constant value (preferably zero). As long as the motor is energised, it rotates the potentiometer in a sense in which the reference voltage is matched closer to the transducer output voltage. When balancing has been attained, the voltage applied to the motor becomes zero so that there no longer takes place any further change of the potentiometer position.

According to a feature of the invention, there may be provided a time element which opens the switch when a predetermined time has elapsed since the closure thereof. The time is then so selected that upon the expiration thereof, as experience has shown, the automatic self-balancing of the circuit arrangement has been completed. In this way, it is impossible that the opening of the switch, by means of which the entire circuit arrangement is brought into its "live" state should be forgotten.

The same is brought about by an electric circuit which monitors the output signal from the subtraction stage and opens the switch when the output signal from the subtraction stage has reached the constant value which is independent of the food batch.

BRIEF DESCRIPTION OF THE DRAWINGS

An exemplified embodiment of the invention will hereinafter be explained in more detail with reference to the drawings.

DESCRIPTION OF THE PREFERRED EMBODIMENTS

Figure 1:
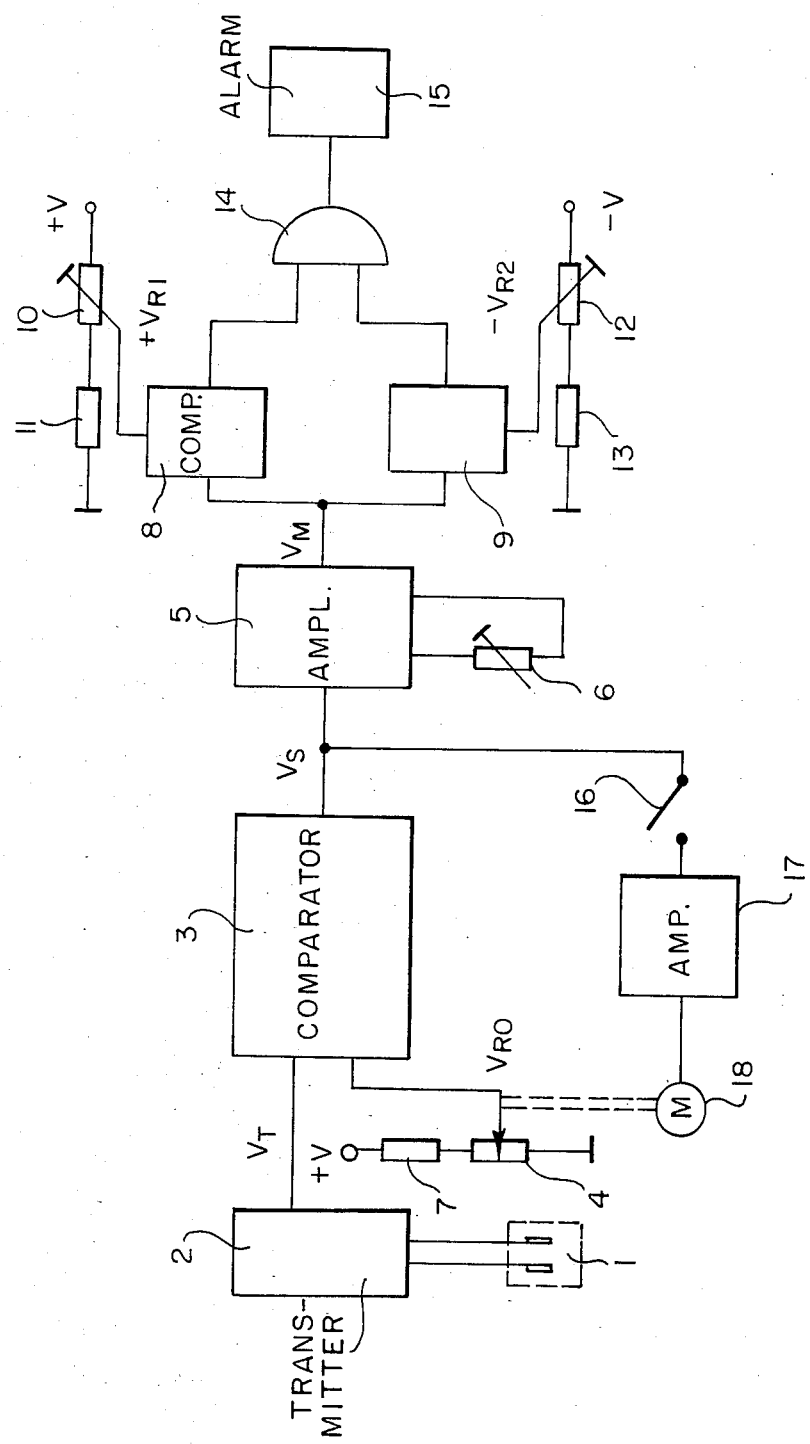
FIG. 1 is a circuit diagram of a first embodiment of the invention.

In the drawing, an inductive conductivity measuring probe, which is provided on the flow path of the milk to be checked, is marked with the reference symbol 1. The measuring probe 1 is connected to a transmitter (transducer) 2, whose output signal $V_T$ is fed to an input of a subtraction stage 3 (a differential amplifier in the exemplified embodiment). A second input of the subtraction stage 3 is connected to the tap (wiper) of a potentiometer 4. The potentiometer 4 is connected across a resistor 7 to a constant voltage $+V$, and the other end is connected to frame.

The output signal $V_S$ from the subtraction stage 3 is fed to a bipolar measuring amplifier 5, the amplifying factor of which is settable by a potentiometer 6. The output of the measuring amplifier 5 is connected to the inputs of two comparators 8, 9.

A potentiometer 10 forms, with a resistor 11, a voltage divider between the voltages $+V$ and O. The tap of the potentiometer 10, to which a positive reference voltage $+V_{R1}$ is applied, is connected to the comparison input of the comparator 8.

A potentiometer 12 forms, with a resistor 13, a voltage divider between the voltages $-V$ and O. The tap of the potentiometer 12, to which a negative reference voltage $-V_{R2}$ is applied, is connected to the comparison input of the comparator 9.

The output signals from the comparators 8, 9 are fed to the two inputs of an OR-gate 14, whose output is connected to an alarm unit 15. (FIG. 1)

Figure 2:
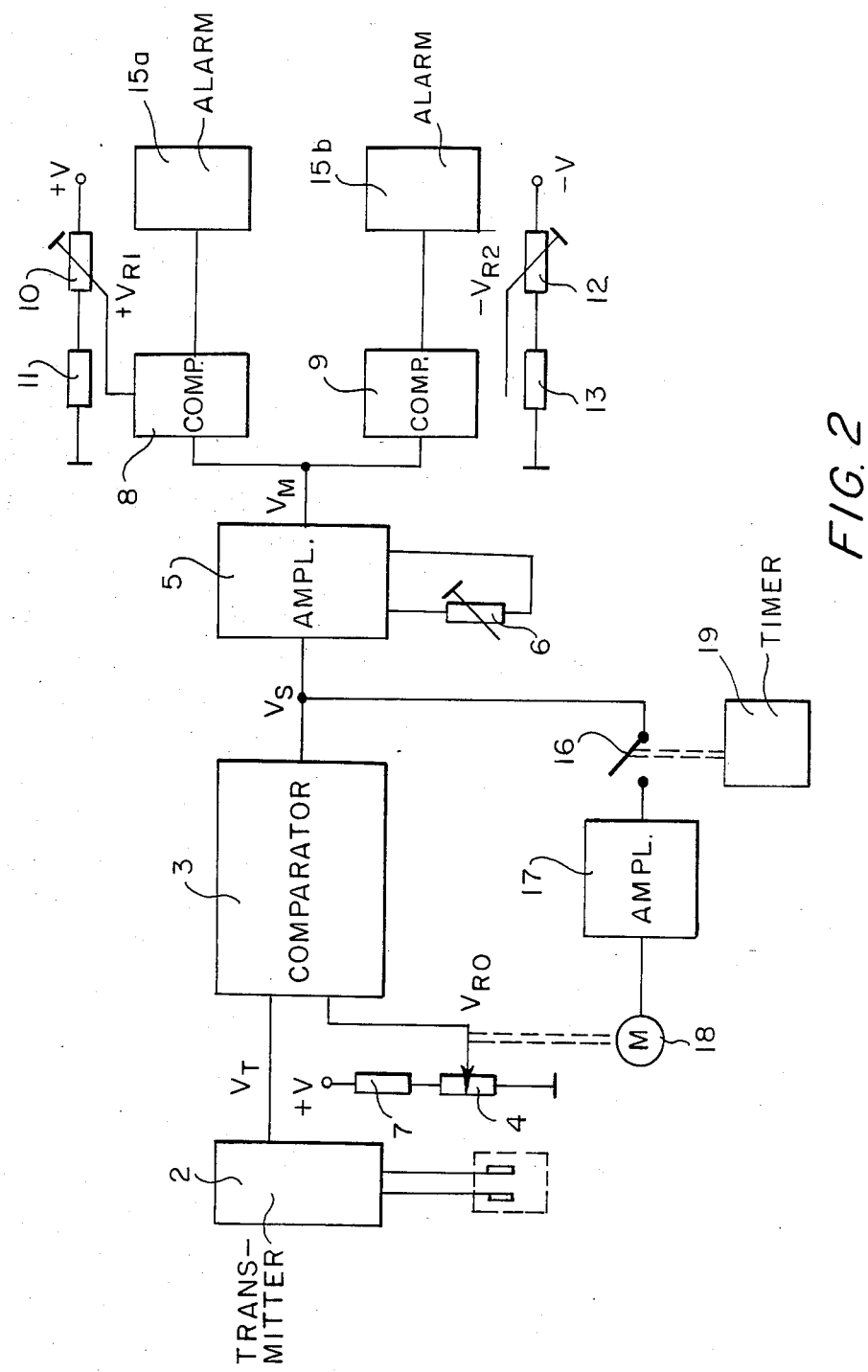
FIG. 2 is a circuit diagram of a second embodiment with separate alarms for the "high" and "low" comparators.

The output signal from the subtraction stage 3 is not only fed to the measuring amplifier 5 but is also applied to an amplifier 17 via a switch 16. (FIGS. 1 and 2) Through the amplifier 17 there is driven a motor 18 which adjusts the wiper of the potentiometer 4.

The operation of the described circuit arrangement is as follows:

Since one can start out from the position that the newly introduced milk is free of contaminants and that the conductivity value measured within this period equals a nominal value $L_S$, the entire circuit arrangement is "standardised" to this nominal value $L_S$ in an initial phase. This is effected in that the reference voltage $V_{R0}$ fed to the second input of the subtraction stage 3 is equalised to the voltage $V_{TS}$ which is emitted by the transmitter 2 at this point in time and which corresponds to the nominal value of the conductivity $L_S$. For this purpose there serves the self-balancing loop consisting of the switch 16, the amplifier 17 and the motor 18 which is coupled to the potentiometer 4. This loop works as follows:

When a new batch of milk is introduced into the line system monitored by the measuring probe 1, the switch 16 is initially closed. The closing of the switch 16 may be forcibly coupled to an action which is necessary in any case upon the introduction of a new batch of milk, for example to the opening of a valve, so that the actuation of the switch 16 cannot be forgotten by inattentive or untrained operators. As long as the voltages $V_{TS}$ and $V_{R0}$, which are applied to the two inputs of the subtraction stage 3, are different, the subtraction stage 3 generates an output voltage. This voltage is applied across the amplifier 17 to the motor 18 which moves the wiper of the potentiometer 4 so that the voltage $V_{R0}$ approximates the voltage $V_{TS}$. When the two voltages have become equal, the output voltage of the subtraction stage 3 is 0; the motor 18 is stopped.

The circuit arrangement has no been standardised to the nominal value $L_S$ of the conductivity of the individual batch. The switch 16 is re-opened. The circuit arrangement is now "live".

The opening of the switch 16, in turn, may be automated, so that no operating errors can occur in this respect either. In the simplest case, the switch 16 is opened by a time element (FIG. 2) which actuates the switch 16 when a specific time, which suffices for balancing, has elapsed IO since the closure thereof. Alternatively, it is possible to open the switch 16 by electronic control when the output voltage of the subtraction stage 3 has become 0.

In the "live" operating state, the circuit works as follows:

The output signal from the subtraction stage 3, which signal is "expanded" by the measuring amplifier 5, deviates in the course of time from the nominal value 0 since the milk flowing through the line system varies in its properties. The band-width or "window", within which conductivity changes are allowable, is defined by the comparison voltages $+V_{R1}$ and $-V_{R2}$ fed to the comparators 8 and 9. If the conductivity of the milk deviates from the nominal value $L_S$ to such a considerable extent that the mentioned window is exceeded in the upward or downward direction, then this is an indication of an unallowable contamination. The respective comparator 8 or 9 then emits an output signal and triggers the alarm via the OR-gate 14.

The functional logic of the circuit upon a batch change of the milk is of decisive importance:

For illustration, let there be assumed a batch change from a milk grade with a high nominal conductivity value $L_{S1}$ (associated transmitter output voltage $V_{TS1}$) to a milk grade with a lower nominal conductivity value $L_{S2} < L_{S1}$ (associated transmitter output voltage $V_{TS2} < V_{TS1}$). The only change in the operating magnitudes of the circuit arrangement upon this batch change is the (automatically performed) "standardisation" to the new nominal conductivity value $L_{S2}$ by the appropriate movement of the slide of the potentiometer 4 and the reduction of the voltage $V_{R0}$ caused thereby. The positions of the potentiometers 6, 10 and 12, in other words the "expansion" of the measurement range, and the allowable window $\Delta_{VT}$ remain unchanged in their absolute value. This means simultaneously that the "relative" window $\Delta_{VT}/V_T$, that is to say the window related to the respective measured quantity $V_T$, does not remain constant but becomes larger as the measured quantity $V_T$ decreases. This is a mode of operation which, in the special field of application of checking liquid food, is not only possible but is definitely advisable. The reason is to be seen in the fact that (at least approximately) the conductivity change caused by a specific contamination quantity is independent of the output conductivity. The "relative" accuracy of the circuit arrangement therefore has to rise as the output conductivity of the milk increaases. The "absolute" accuracy has to be the same over the entire measurement range of the circuit arrangement.

This peculiarity in connection with the checking of liquid food is atypical of other measuring operations, where generally a substantially constant relative measurement accuracy is desired. However, it opens up the possibility of providing unproblematical checking which is performed with the described circuit arrangement and which can be effected fully automatically or by untrained staff.

The allowable band-width, the "window" $\Delta_{VT}$, does not have to be symmetrical with respect to the nominal value $V_{TS}$. On the contrary, it is recommendable that the allowable deviation towards higher values $\Delta_{VT}+$ should be smaller than the allowable deviation towards lower values $\Delta_{VT}-(\Delta_{VT}=\Delta_{VT}++\Delta_{VT}-)$. For a deviation of the conductivity towards higher values is equivalent to a contamination of the milk by means of acids or lyes, whereas a reduction of the conductivity generally points to a dilution of the milk by means of water which, in any event as regards health, is irrelevant and is therefore more acceptable.

The potentiometers 6, 10 and 12 are only adjusted when it is intended to use the circuit arrangement for an entirely different type of liquid, for example if beer rather than milk is to be checked. This initial setting, which as a rule has to be made only once in respect of each installed circuit arrangement, can then be carried out by an expert.

Figure 3:
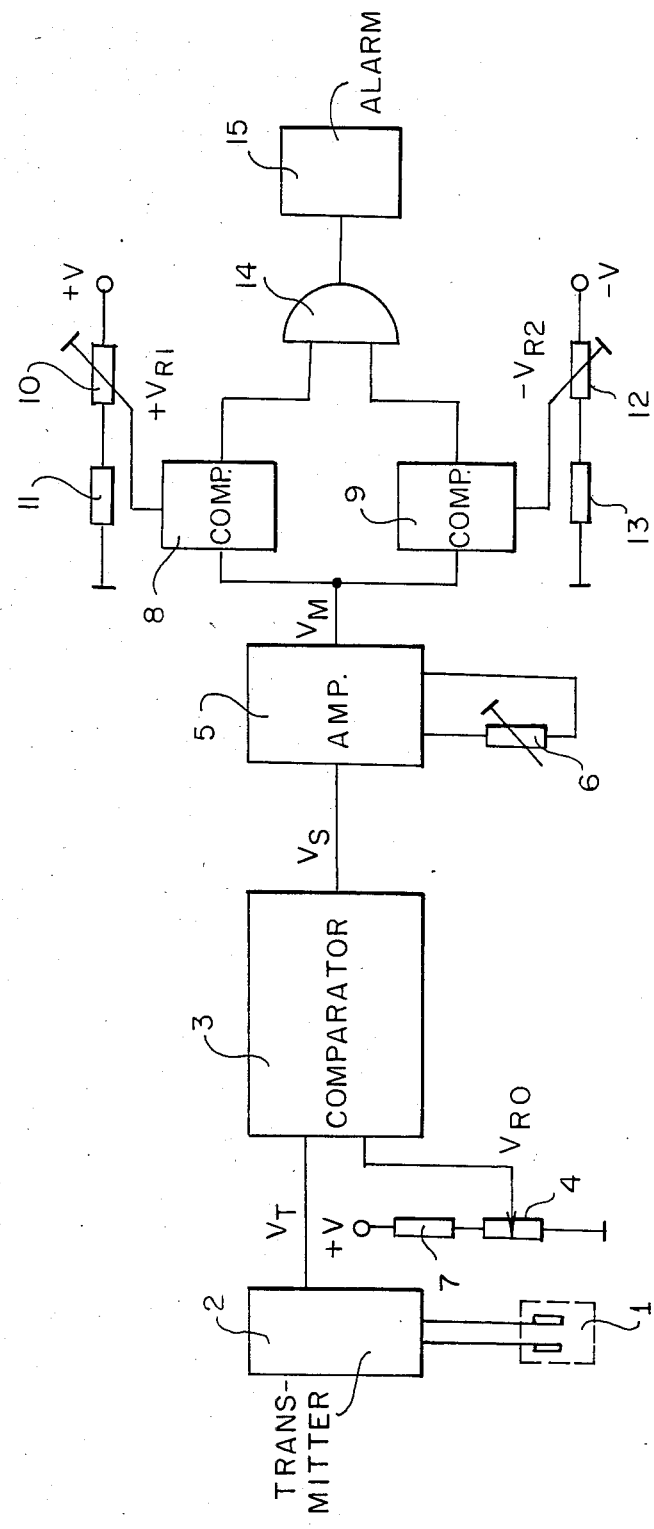
FIG. 3 is a circuit diagram of a third embodiment with manual setting of the reference voltage.

In a second exemplified embodiment, which is shown in FIG. 3, the "standardisation" of the circuit arrangement to the nominal conductivity value $L_S$ is not effected automatically as is the case in the above-described exemplified embodiment. Here, following the entry of a new batch of liquid into the monitored system, the potentiometer 4 is adjusted by hand until a visual display (e.g. a measuring instrument), which is integrated in the measuring amplifier 5, reveals that the output signal from the subtraction stage 3 drives the measuring amplifier 5 to the centre of its measurement range.

In a third exemplified embodiment of the circuit arrangement, which is not shown, the "standardisation" to the nominal conductivity value $L_S$ is effected in such a way that the output voltage of the subtraction stage 3 is brought to a constant value which deviates from 0 and is not specific to a batch. The downstream components 5, 8, 9, 14, 15 can then be operated unipolarly and so as to be substantially balanced with respect to the output voltage of the subtraction circuit 3.

I claim:

1. A circuit arrangement for checking liquid food for contaminants which comprises
   (a) a conductivity measuring probe (1) which is adapted to be placed in the liquid food to be checked,
   (b) a transducer (2) which generates from the output signal from said measuring probe a voltage ($V_T$) which is a measure of the conductivity detected,
   (c) a substraction stage (3) in which an individual reference voltage ($V_{R0}$) adapted to the type of food to be checked is subtracted from the transducer voltage ($V_T$) in such a way that the output signal ($V_S$) from the subtraction stage (3) has a constant value which is independent of the food batch,
   (d) a measuring amplifier (5) which amplifies the output signal ($V_S$) from the subtraction stage (3) to an extent that is independent of the food batch,
   (e) a first comparator (8) which compares the output signal ($V_M$) from the measuring amplifier (5) with a first comparison voltage ($+V_{R1}$) which represents an upper allowable conductivity nominal value ($L_S$) deviation which is independent of the food batch, said first comparator (8) triggering an alarm (15) if the first comparison voltage ($+V_{R1}$) is exceeded, and
   (f) a second comparator (9) which compares the output signal ($V_M$) from the measuring amplifier (5) with a second comparison voltage ($-V_{R2}$) which represents a lower allowable conductivity nominal value ($L_S$) deviation which is independent of the food batch, the second comparator (9) triggering an alarm (15) if the second comparison voltage ($-V_{R2}$) is not attained.

2. A circuit arrangement as set forth in claim 1 wherein a separate alarm unit (15) is associated with each comparator (8,9).

3. A circuit arrangement as set forth in claim 1 wherein the output signals from the two comparators (8,9) are fed via an OR-gate (14) to the same alarm unit (15).

4. A circuit arrangement as set forth in claim 1 wherein the upper allowable conductivity nominal value ($L_S$) deviation represented by the first comparison voltage ($+V_{R1}$) is less than the lower allowable conductivity nominal value ($L_S$) deviation represented by the second comparison voltage ($-V_{R2}$).

5. A circuit arrangement as set forth in claim 1 wherein the unit generating the reference voltage ($V_{R0}$) fed to the subtraction stage (3) is actuatable by hand, and there is provided a visual display which gives a display when the output voltage ($V_S$) of the subtraction stage (3) has reached the constant value which is independent of the food batch.

6. A circuit arrangement as set forth in claim 1 wherein the unit generating the reference voltage ($V_{R0}$) fed to the subtraction stage (3) comprises a self-balancing loop (4, 17, 18) which is insertable via a switch (16) between the output of the subtraction stage (3) and the reference input of the subtraction stage (3), the switch (16) being closed when a new liquid food batch is introduced into the monitored system until balancing is completed and then being re-opened.

7. A circuit arrangement as claimed in claim 6 wherein the self-balancing loop comprises
   (g) an amplifier (17), to which the output signal from the subtraction stage (3) can be fed,
   (h) a motor (18) which is connected to the output of the amplifier (17), and
   (i) a potentiometer (4) which forms part of a voltage divider and whose wiper is mechanically coupled to the motor (18).

* * * * *